(12) United States Patent
Griesser et al.

(10) Patent No.: US 9,576,502 B2
(45) Date of Patent: Feb. 21, 2017

(54) UNIVERSAL AED TRAINING ADAPTER

(75) Inventors: Hans Patrick Griesser, Bainbridge Island, WA (US); Dennis E. Ochs, Bellevue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 290 days.

(21) Appl. No.: 14/004,603

(22) PCT Filed: Feb. 28, 2012

(86) PCT No.: PCT/IB2012/050923
§ 371 (c)(1),
(2), (4) Date: Sep. 11, 2013

(87) PCT Pub. No.: WO2012/127340
PCT Pub. Date: Sep. 27, 2012

(65) Prior Publication Data
US 2014/0004494 A1      Jan. 2, 2014

Related U.S. Application Data

(60) Provisional application No. 61/466,315, filed on Mar. 22, 2011.

(51) Int. Cl.
*G09B 23/28* (2006.01)
*A61N 1/39* (2006.01)

(52) U.S. Cl.
CPC ............. *G09B 23/28* (2013.01); *A61N 1/3968* (2013.01); *A61N 1/3993* (2013.01); *G09B 23/288* (2013.01)

(58) Field of Classification Search
CPC ..... G09B 23/28; G09B 23/2883; G09B 23/32; A61N 1/3968; A61N 1/3993
See application file for complete search history.

(56) References Cited

U.S. PATENT DOCUMENTS

| | | | |
|---|---|---|---|
| 5,275,572 A | 1/1994 | Ungs et al. | |
| 5,611,815 A | 3/1997 | Cole et al. | |
| 5,662,690 A | 9/1997 | Cole et al. | |
| 5,993,219 A | 11/1999 | Bishay | |
| 6,125,298 A * | 9/2000 | Olson | A61N 1/39 607/5 |
| 6,336,047 B1 | 1/2002 | Thu et al. | |
| 7,715,913 B1 | 5/2010 | Froman et al. | |
| 2004/0157199 A1* | 8/2004 | Eggert | G09B 23/30 434/262 |
| 2009/0035740 A1 | 2/2009 | Reed et al. | |

FOREIGN PATENT DOCUMENTS

| | | |
|---|---|---|
| CN | 2242497 Y | 12/1996 |
| EP | 1852144 A2 | 11/2007 |
| JP | H04296893 A | 10/1992 |
| JP | 2000176025 A | 6/2000 |
| JP | 2010508940 A | 3/2010 |
| WO | 2008059396 A1 | 5/2008 |

\* cited by examiner

*Primary Examiner* — Timothy A Musselman

(57) ABSTRACT

A training adapter (28) for an automated external defibrillator (AED) (10) which provides for safe training use of any AED. The training adapter includes a circuit which ensures that any defibrillation voltage/current is shunted away from the trainee, training electrodes (26), and patient simulation equipment. The training adapter simultaneously provides to the AED a simulated patient ECG signal which causes the AED to operate as if an actual cardiac rescue were occurring, thus heightening the realism of the training experience.

19 Claims, 6 Drawing Sheets

UNIVERSAL AED TRAINING ADAPTER

CROSS-REFERENCE TO PRIOR APPLICATIONS

This application is the U.S. National Phase application under 35 U.S.C. §371 of International Application No. PCT/IB2012/050923, filed on Feb. 28, 2012, which claims the benefit of U.S. Provisional Patent Application No. 61/466,315, filed on Mar. 22, 2011. These applications are hereby incorporated by reference herein.

Aspects of this invention relate generally to external defibrillator training, and more specifically to devices which allow external defibrillators to be safely used for training and to a method for training a user to operate an external defibrillator.

Abnormal heart activity, such as ventricular fibrillation, may be returned to a normal sinus rhythm by applying an electric current to the heart using an external defibrillator. In sudden cardiac arrest, the patient is stricken with a life threatening interruption to the normal heart rhythm, typically in the form of VF or VT that is not accompanied by spontaneous circulation (i.e., shockable VT). In VF, the normal rhythmic ventricular contractions are replaced by rapid, irregular twitching that result in ineffective and severely reduced pumping by the heart. If normal rhythm is not restored within a time frame commonly understood to be approximately 8 to 10 minutes, the patient will die. Conversely, the quicker that circulation can be restored (via CPR and defibrillation) after the onset of VF, the better the chances that the patient will survive the event.

FIG. 1 is an illustration of a defibrillator 10 being applied by a user 12 to resuscitate a patient 14 suffering from cardiac arrest. Such external defibrillators may be manual, automatic or semi-automatic. The defibrillator 10 is shown in the form of an automated external defibrillator (AED) capable of being used by a first responder user 12. The user 12 deploys the defibrillator 10 by turning it on, plugging the defibrillation electrode connector into a socket in defibrillator 10, and by connecting the electrode pads 16 across the patient 14 torso. The defibrillator analyzes the patient's ECG to determine whether a defibrillating shock is necessary. If so, the defibrillator 10 prompts the user 12 to press a button to deliver the shock.

The scenario illustrated by FIG. 1 is experienced relatively infrequently by first responders, especially by lay persons who first arrive at the stricken patient. Although most AEDs offer voice prompting to guide an untrained user through the rescue steps, it is desirable to teach operators of all types of external defibrillators to use actual defibrillation equipment in a realistic training environment that simulates and approximates actual defibrillator use procedures and conditions. Because timeliness of therapy is so important to survival from sudden cardiac arrest, effective and realistic training programs are needed. Such programs are ideally simple and inexpensive enough that they can be used in CPR courses offered to the populace.

Accordingly, some external defibrillators incorporate a training mode in addition to a therapy mode in order to provide an in situ training opportunity to potential users. Alternatively, training devices that simulate defibrillator operation are used to provide training to potential users. Because defibrillating voltage is dangerous to users and bystanders, it is important that both types of training device merely simulate electrotherapy. In each case, the defibrillator electrodes are attached to a human-simulating training apparatus, such as a mannequin, and are not electrically connected to the defibrillator. Examples of external defibrillators having both therapy modes and training modes are provided in U.S. Pat. No. 7,715,913, U.S. Pat. No. 5,611,815, and in U.S. Pat. No. 5,662,690, the specifications of which are incorporated herein by reference.

In order to maximize effectiveness, defibrillator training should be interactive. The training apparatus should advance its operational state like an actual defibrillator as the user progresses through the rescue. Changes in operational state in known defibrillators are triggered by user actions such as powering the defibrillator on, connecting the electrode plug to the defibrillator, attaching the defibrillator electrodes to a patient and sensing the patient's ECG, and by pressing a shock button. Because no actual patient is used during training, the operational state changes in a training defibrillator may be based on other inputs, such as elapsed time, detecting the insertion of a training electrode into an electrode interface, manipulation of the defibrillator controls by the user, or by signals generated by a remote device operated by the training supervisor.

Interactive training generally begins with the operator being instructed to call emergency medical services, expose the chest, open and place one or more training electrodes onto a particular position on a mannequin. The operator's proper electrode placement and positioning generally triggers an operational state change in the training mode of the defibrillator—the defibrillator operator, for example, next being instructed that the defibrillator is analyzing, and not to touch the patient. Several types of sensing systems have been developed to indicate proper positioning of training electrodes on mannequins. For example, conductive adapter strips for use with mannequins are described in U.S. Pat. No. 5,993,219. In another example, conductive objects are embedded in mannequins.

FIG. 2 illustrates a prior art training system comprising a defibrillator 10, electrode pads 26 and a training mannequin 24. The prior art defibrillator 10 is either a rescue defibrillator which has an internal training mode of operation or a dedicated training defibrillator which has no defibrillating capacity. A conductive strip 22 is located on the mannequin such that when the pads 26 are placed correctly, defibrillator 10 senses the resulting impedance change and the training scenario progresses.

Many defibrillators lack any internal training mode. One who wishes to familiarize a user with the operation of such a defibrillator must obtain a separate training defibrillator that simulates that particular defibrillator. This solution is expensive, inconvenient and restricts the training opportunities to that particular make and model of defibrillator.

According to one aspect of the present invention, a universal training adapter system for use with an external defibrillator is described which allows the safe use of the external defibrillator for training. The system is advantageous in that it may be used with any defibrillator. An adapter is disposed between the defibrillator and a training device such as a mannequin to sense when electrodes are properly positioned on the training device. The adapter, senses the proper positioning of electrodes, and then electrically connects an ECG simulator and shunt resistor to the defibrillator electrode path. The defibrillator can then sense the ECG and arm itself to deliver a shock exactly as if an actual patient with sudden cardiac arrest were attached to it. A shunt resistor attached to the adapter absorbs the resulting defibrillating shock energy. Because the shock bypasses the training device, the trainee is never exposed to hazardous defibrillation voltage.

According to another aspect of the present invention, a universal training adapter for use with an external defibrillator is described which allows the safe use of the defibrillator for training. The adapter serves as a control hub for selectively connecting electrodes, defibrillator, an ECG simulator and a shunt resistor as the training scenario progresses. The ECG simulator or shunt resistor can be located external to the adapter, or can be integrated internally to the adapter casing. The adapter can further be configured to attach either training or rescue electrodes in a connection dock. The adapter may further comprise a user interface with buttons and display for setting up the training scenario prior to the training session. Control may optionally be provided to the adapter via remote control.

According to another aspect of the present invention, a method for using an external defibrillator in its rescue mode to train a user. The method comprises the steps of sensing the proper placement of electrodes on a simulated patient, automatically connecting an ECG simulator to a defibrillator in response to the sensing step, providing a simulated ECG signal from the ECG simulator to the defibrillator, and shunting and dissipating the defibrillation energy delivered by the defibrillator responsive to the providing step away from the simulated patient. The training method can be adjusted for various rescue scenarios by setting up the simulated patient characteristics prior to the training, using an optional selection and display device.

IN THE DRAWINGS

Figure 1:
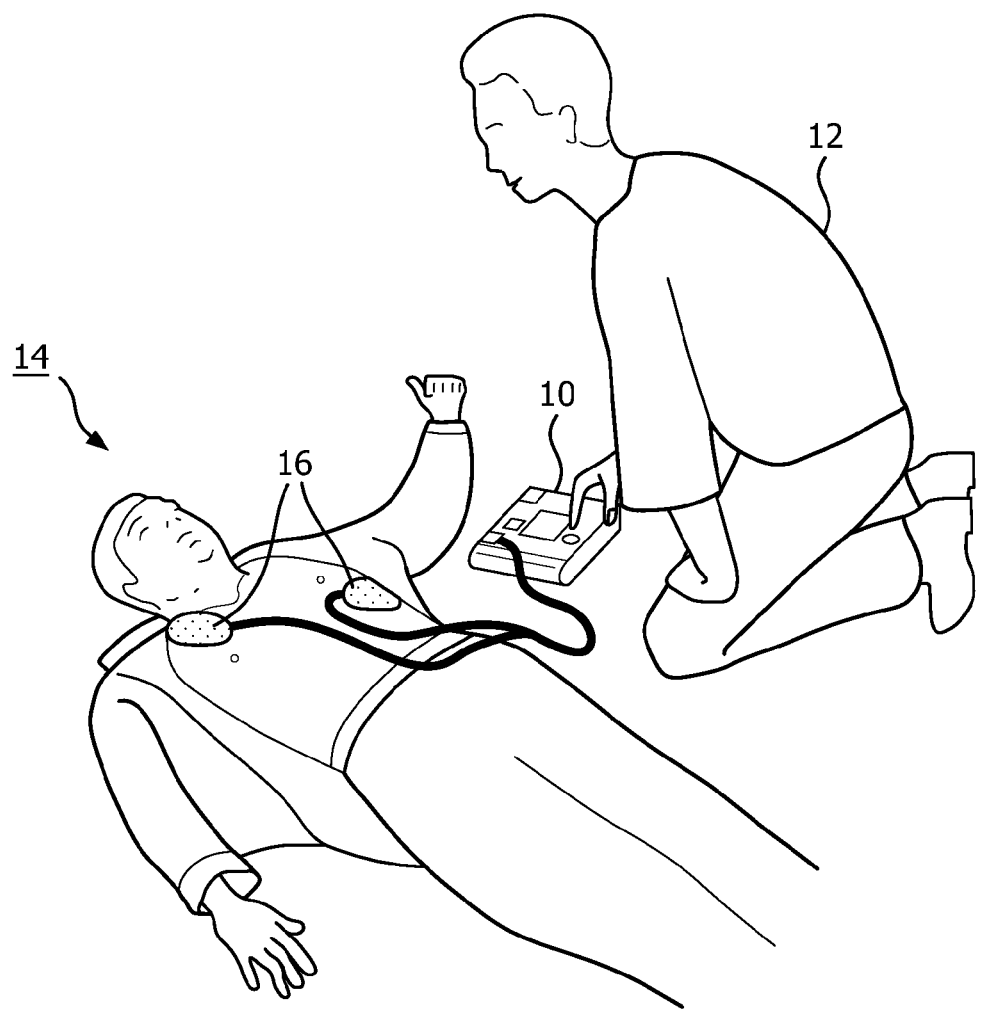
FIG. 1 is an illustration of a defibrillator being applied to a patient suffering from cardiac arrest.
Figure 2:
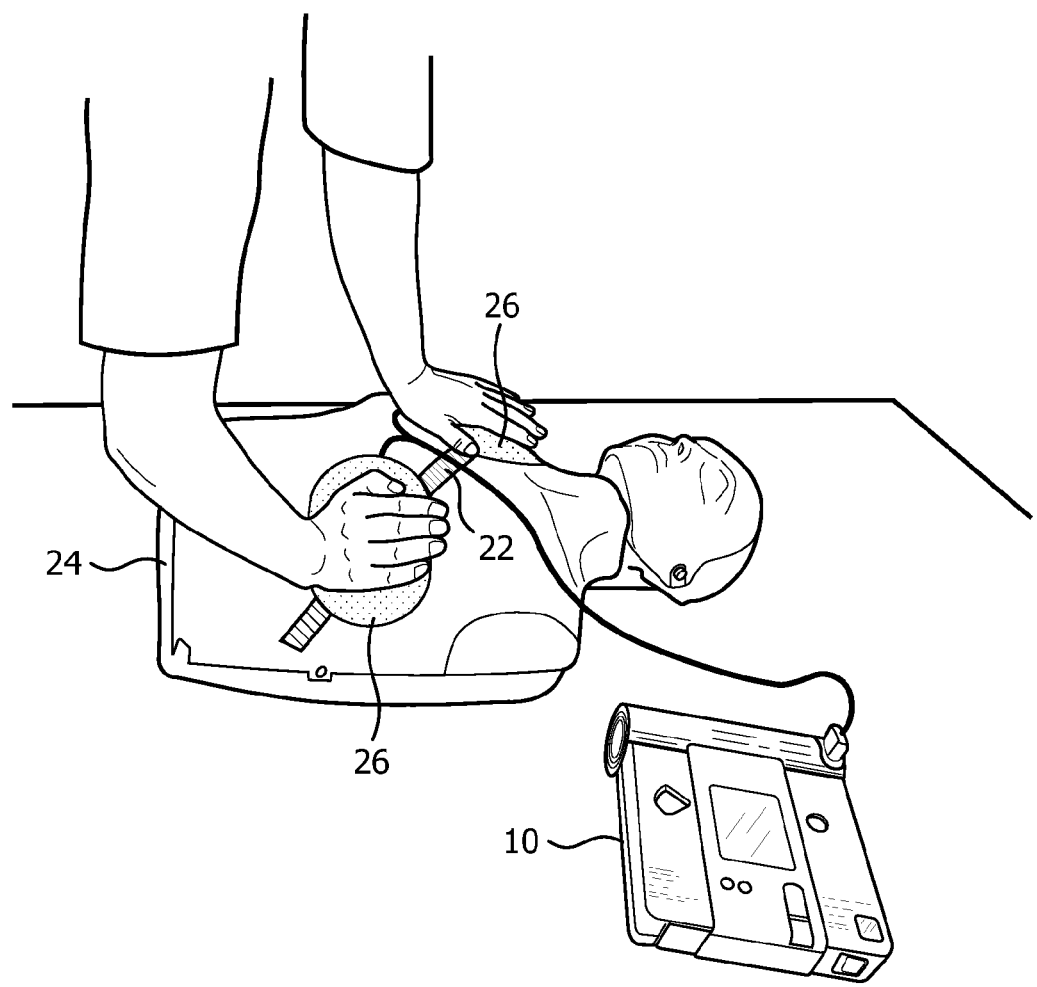
FIG. 2 is an illustration of a prior art training system in use with either a prior art defibrillator having an internal training mode or with a dedicated defibrillator simulator trainer.
Figure 3:
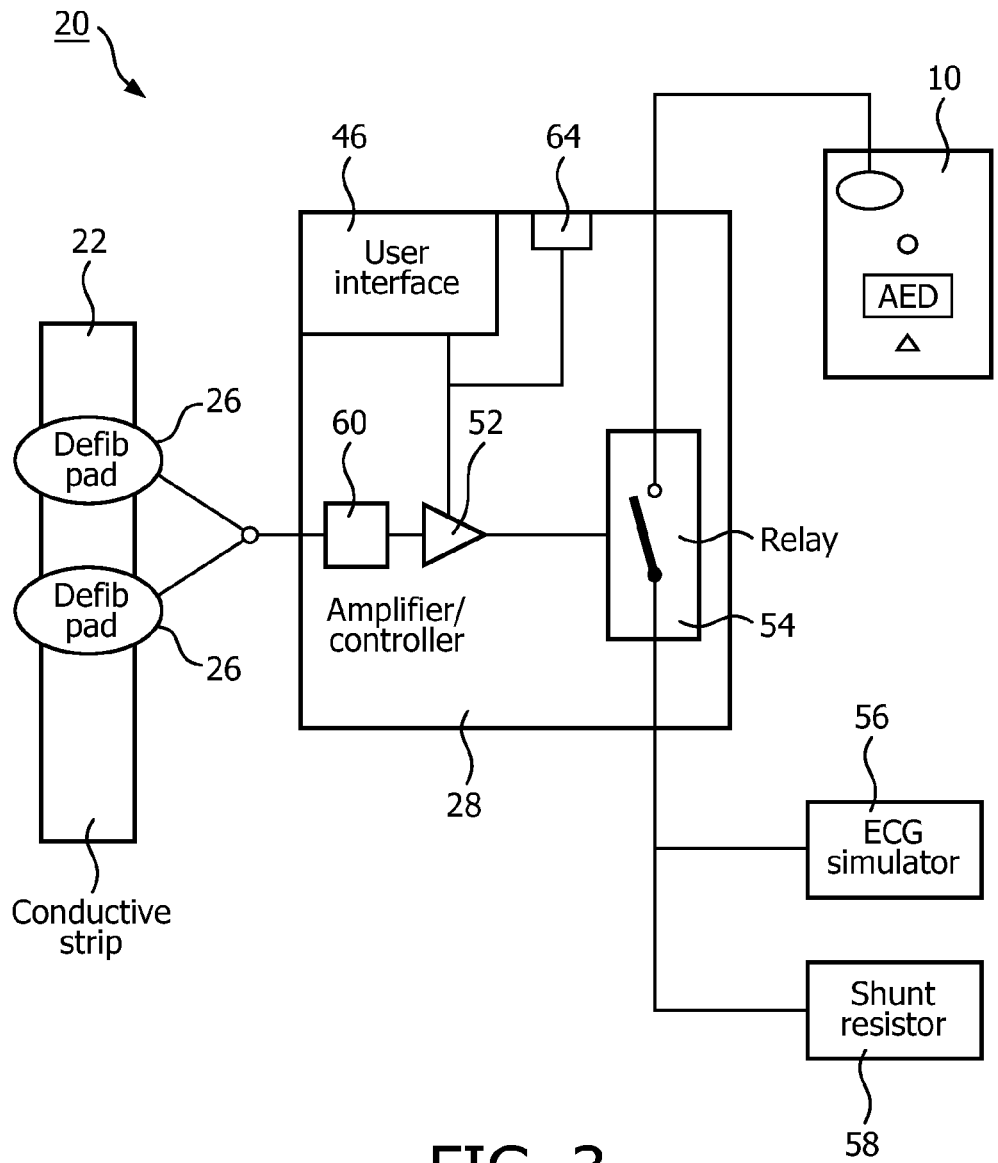
FIG. 3 illustrates a block diagram of the training adapter system in accordance with the principles of the present invention.

Now turning to the figures, FIG. 3 illustrates a training adapter system 20 constructed in accordance with the principles of the present invention. For purposes of the discussion that follows, the defibrillator 10 is configured as an AED, and is designed for small physical size, light weight, and relatively simple user interface capable of being operated by personnel without high training levels or who otherwise would use the defibrillator 10 only infrequently. Although the present embodiment of the invention is described with respect to application in an AED, other embodiments include application in different types of defibrillators, for example, manual defibrillators, and paramedic or clinical defibrillators. All types are characterized in that none have its own internal training mode of operation.

The system further comprises a training adapter 28 that is connected to standard electrode connector on defibrillator 10. A universal connector is envisioned which comprises electrode plug adapters which interface with all AED manufactures. Training adapter 28 comprises a relay 54 to which one junction is connected to the defibrillator 10 electrode connector. A second junction on relay 54 is connected to both of an ECG simulator 56 and a shunt resistor 58. Relay 54 is controlled by a controller 52 whose operating parameters are established via a user interface 46. An optional safety resistor 60 provides redundant protection from defibrillation leakage voltages. As will be described in further detail in FIG. 5, the training adapter 28 electronics are disposed inside an insulated casing having protected electrical connectors to external components. FIG. 3 shows ECG simulator 56 and shunt resistor 58 residing outside training adapter 28. In this embodiment, ECG simulator 56 and shunt resistor 58 may be integrated together in a commercial defibrillator training simulator such as the IMPULSE 3000 manufactured by Dynatech Corporation. In an alternative embodiment, either ECG simulator 56 and shunt resistor 58 may be incorporated into training adapter 28 as an integrated component.

Relay 54 is of construction robust enough to repeatedly pass defibrillation currents ranging from about 10 A-45 A and to withstand defibrillation voltages of 1000V-4000V across its contacts. Relay 54 should also be disposed to hold off defibrillation voltage from its control junction.

Controller 52 is shown connected to an input received from a pair of defibrillation electrode pads 26, which may be either training electrodes having reusable conductive gel on the pads or regular rescue electrodes. Underlying electrode pads 26 is a conductive strip 22 which resides on a standard training mannequin 24. The input may be a change in impedance across pads 26 as they are connected, or may be by other known methods of sensing pads placement. In an alternate embodiment, controller 52 may be connected to an operating signal from remote relay control 64 in communication with a remote control 62. The remote operating signal replaces and simulates the input from the pair of pads 26. The remote signal may be initiated by a training supervisor.

In operation, controller 52 selectively operates relay 54 in response to an input from electrode pads 26 or equivalent. Relay 54 in effect simulates to the connected defibrillator 10 that electrodes have been attached to a patient. When relay 54 is closed, a simulated ECG signal generated from ECG simulator 56 is passed to defibrillator 10. Defbrillator 10 analyzes the ECG signal. If the analysis indicates that a shock is appropriate, defibrillator 10 arms itself and advises that it is ready to shock according to its operating protocol. The training user then intiates the shock via button press or other means. The defibrillating shock energy passes through relay 54, and is dissipated in shunt resistor 58. Depending on subsequent ECG simulator 56 signals and defibrillator 10 rescue protocols, the process may be repeated until the training scenario is complete.

Figure 4:
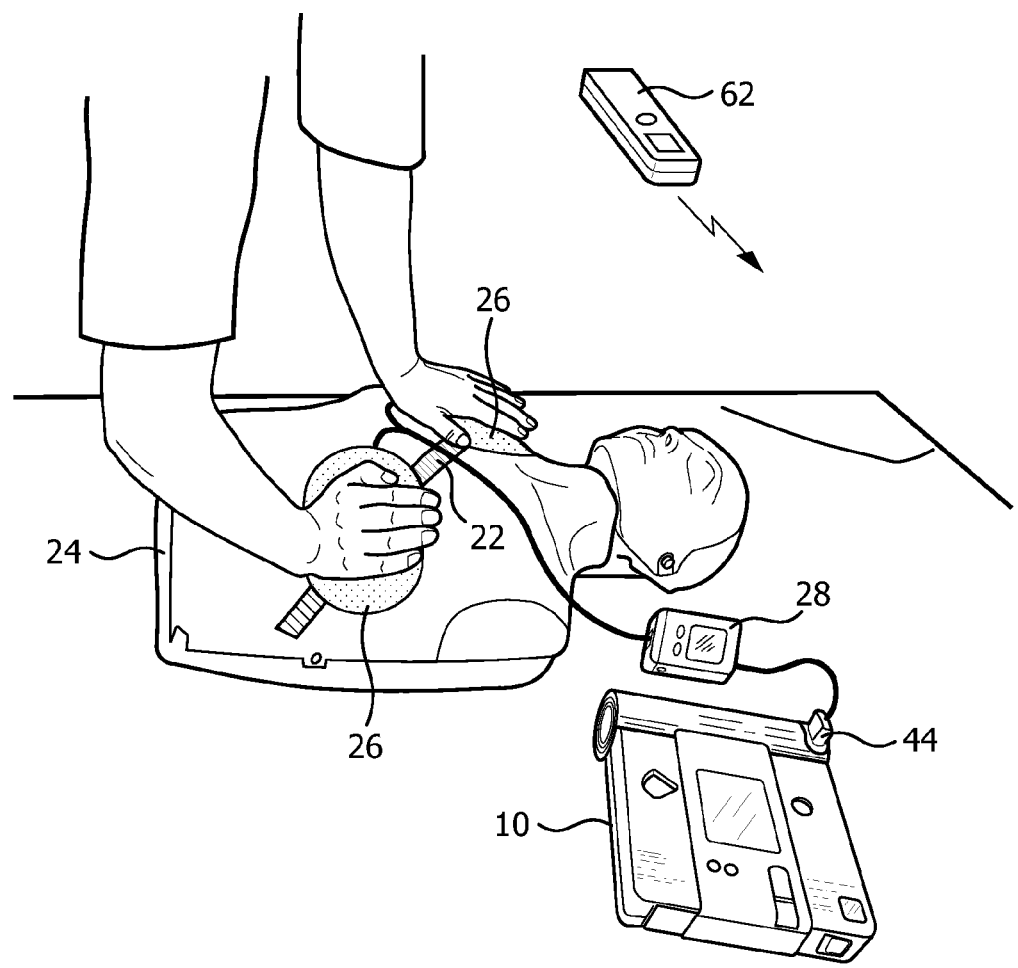
FIG. 4 is an illustration of a training adapter system constructed in accordance with the principles of the present invention, which can be used with a prior art defibrillator.

FIG. 4 illustrates embodiments of the training adapter system 20, in particular as to the means for detecting and signaling to the adapter 28 that electrode pads 26 have been properly placed on a simulated patient. Direct input means to training adapter 28 may be from rescue or training defibrillator electrode pads 26 via the electrode lead wires and electrode plug (not shown). Impedance changes caused by properly placing the electrode pads 26 on top of a conductive strip 22 that has been installed on a training mannequin 24. Alternatively, a training supervisor who is overseeing the trainee's electrode placement actions may operate a remote control 62 to wirelessly signal training adapter 28. Once electrode pads 26 have been properly placed on a simulated patient, the supervisor will press a button on the remote control 62 to initiate the signal.

Training adapter 28 responds to the input means by closing relay 54, which connects an electrical pathway from ECG simulator 56 to defibrillator 10 through electrode connector 44. In response to a treatable cardiac rhythm generated by ECG simulator 56, defibrillator 10 arms and delivers a shock to shunt resistor 58 via connector 44 and relay 54. In the FIG. 4 embodiment, both ECG simulator 56 and shunt resistor 58 reside inside training adapter 28. It can be seen from FIG. 4 that any type of defibrillator may be used with the adapter system as long as a properly mating electrode connector 44 is used.

Figure 5:
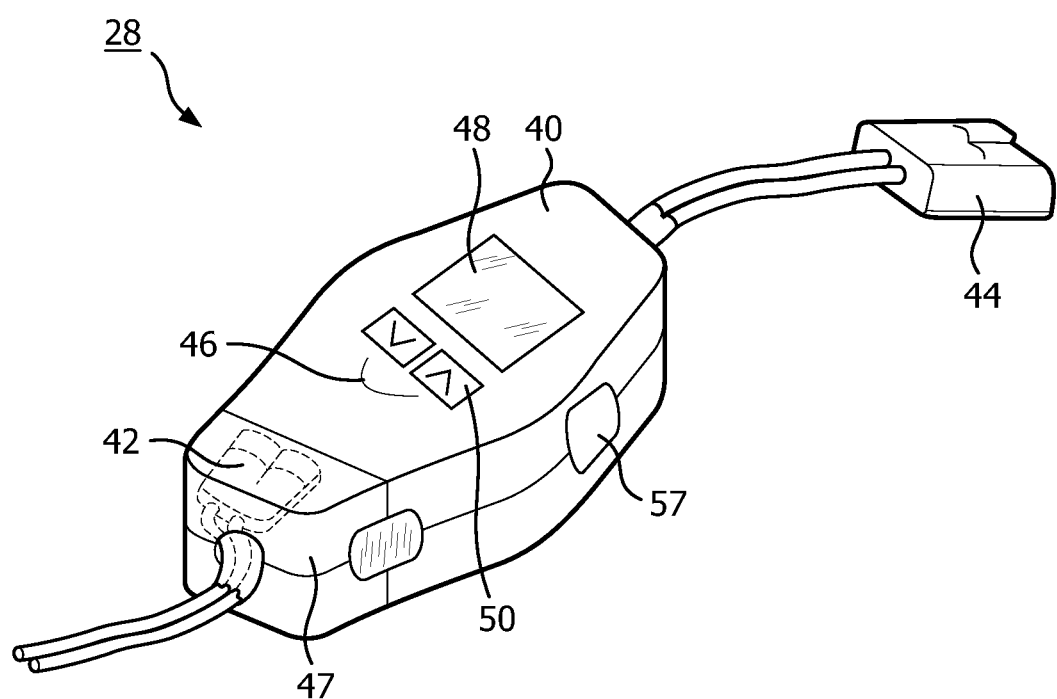
FIG. 5 illustrates an embodiment of a training adapter apparatus of the present invention.

FIG. 5 illustrates another and more detailed embodiment of training adapter 28. Adapter electronics reside inside an electrically insulated casing 40. All electrical interfaces are protected from stray defibrillation voltages by suitable non-conductive plugs and wire sleeves. For example, casing 40 may include a covered port 57 for passing an electrical cable from internal relay 56 to an optional external ECG simulator 56 and shunt resistor 58. Also shown is a protected clamshell port 47 for installing a defibrillator electrode connector 42 to the adapter 28 electronics. In addition to preventing stray voltages from casing 40, the clamshell port 47 places the connector 42 out of view to a trainee. Thus the only defibrillator connector in sight of and available to a trainee is connector 44 for attaching in the normal manner to a defibrillator. Connector 42 being out of sight of and unavailable to a trainee, confusion is reduced and training realism is enhanced. Clamshell port 47 may also be used to replace a battery power supply to adapter 28.

Training adapter 28 optionally comprises a user interface 46. User interface 46 further comprises a display 48 and user selector button(s) 50. For embodiments which integrate the ECG simulator 56 within the training adapter case 40, display 48 and user selector button 50 may be used to set up the training scenario before training begins. For example, the user interface 46 may be used to select a series of arrhythmia outputs from ECG simulator 56 prior to and following defibrillation shocks. Display 48 may also be disposed to indicate operating parameters such as training progress, elapsed time, battery state, or remote control connectivity.

Figure 6:
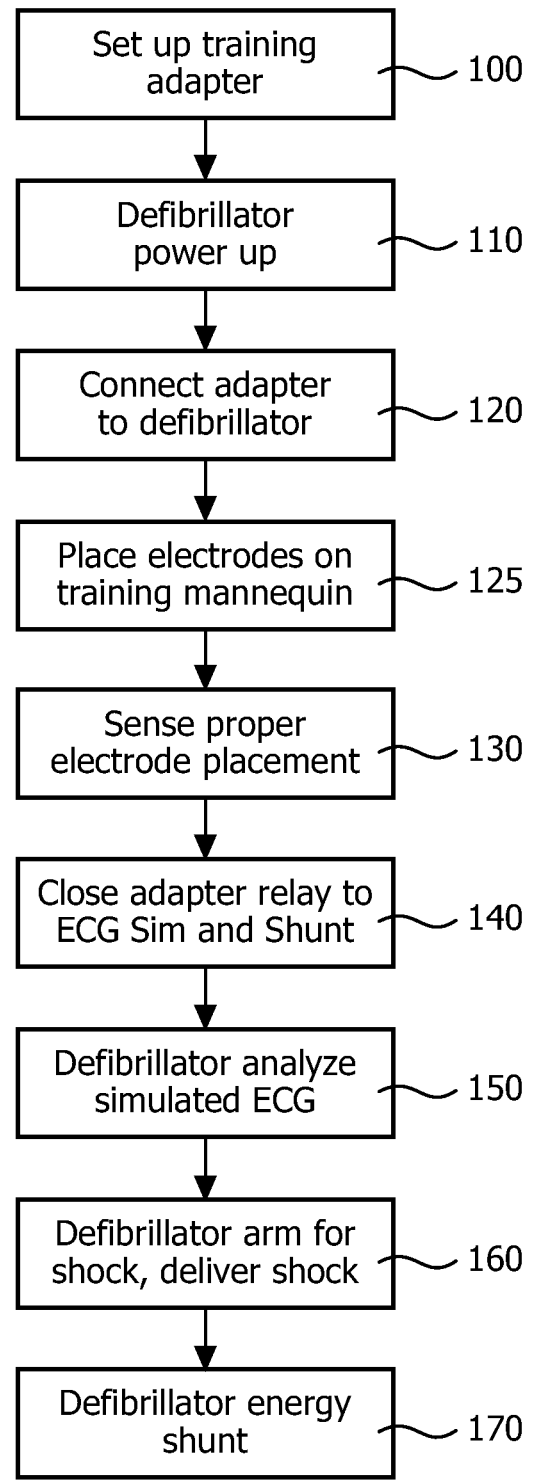
FIG. 6 illustrates a flow chart of a method for using a standard AED with the training system of the present invention to train a user in defibrillating a patient.

FIG. 6 illustrates a method of conducting defibrillation training using a defibrillator in rescue mode with a training adapter system of the present invention. Prior to beginning a training session, the training adaptor and/or the ECG simulator is set up in step 100. An ECG training scenario is selected via either user interface 46 or on the external ECG simulator 56. Training electrodes 26 are installed on adapter 28, and any mannequin training aids are prepared.

Defibrillator training begins at step 110 in the manner usual to actual rescues. The defibrillator 10 is powered up to begin its rescue protocol, and begins by issuing verbal prompts, such as to call 911 and to connect the electrodes. In response to the prompts, the trainee connects the electrode connector 44 to the defibrillator 10 at step 120. Some types of defibrillators 10 sense the connector 44 connection and advance to subsequent verbal prompts to place electrodes on the patient. At step 125, the trainee responds by applying the supplied electrode pads 26 to the training aid, such as the mannequin.

Training adapter 28 detects when the electrode pads 26 are properly placed on the training aid at step 130. Several different means of detecting may be used such as for example by sensing an impedance change caused by pads 26 placed across conductive strip 22, by magnetic sensors installed in the mannequin, or by a supervisor trainer input by button or remote control.

In step 140, controller 52 operates relay 54 to close in response to proper electrode pads placement. The relay closure connects defibrillator 10 to ECG simulator 56 and shunt resistor 58.

At step 150, the defibrillator 10 analyzes the ECG signal received from ECG simulator 56 in its normal manner to determine whether a defibrillating shock is indicated. If so, the defibrillator arms itself by charging its high voltage electrotherapy system and prompts the user to deliver a shock. The trainee user presses the shock button to deliver therapy at step 160.

The training adapter 28 operates at step 170 to divert the delivered shock energy away from the electrode pads 26, training mannequin 24, and trainee/user 12. The delivered shock instead passes from defibrillator 10 through connector 44 and relay 54 into shunt resistor 58, thereby bypassing any electrical path to the electrode pads 26. In case of a failure of an internal component, an optional safety resistor 60 disposed inside the adapter 28 and in series with electrode pads 26 may provide a second line of protection.

Alternatives to the above-described training adapter are envisioned which fall within the scope of the claimed invention. For example, the training adapter 28 may be part of a semi-disposable set of training electrodes, or may be completely reusable. Remote operation may be by wireless radio frequency, by series infrared signals, or by cabled connection. In addition, the progress and recording of the training session may be conducted in a step 180 in parallel to the steps of the training use.

What is claimed is:

1. A training adapter system for a defibrillator comprising:
   a pair of patient electrodes;
   a detector operable to detect the proper placement of the patient electrode pair on a simulated patient and to provide a signal corresponding to the detection;
   a connector disposed for electrical connection with a defibrillator;
   an ECG simulator;
   a defibrillation energy shunt resistor; and
   a controller which electrically connects the connector with the ECG simulator and the shunt resistor in response to the signal from the detector,
   thereby bypassing any electrical path from the defibrillator to the pair of patient electrodes.

2. The training adapter system of claim 1, wherein the detector further comprises an electrically conductive path disposed between proper electrode placement locations on the simulated patient and further wherein the signal is the closing of a circuit enabled by the attachment of the patient electrodes to the proper electrode placement locations.

3. The training adapter system of claim 1, wherein the detector further comprises a user control for providing the signal to the controller.

4. The training adapter system of claim 3, wherein the user control is a remote control.

5. The training adapter system of claim 1, wherein the controller further
   comprises a relay which closes to electrically connect the connector with the ECG simulator and the shunt resistor in response to the signal.

6. The training adapter system of claim 1, wherein the controller further
   comprises an electrode socket for replaceably connecting the pair of patient electrodes.

7. The training adapter system of claim 1, wherein all electrical pathways connecting the defibrillator, controller, ECG simulator, and shunt resistor are shielded.

8. The training adapter system of claim 1, wherein the ECG simulator further comprises a control for selecting one of a plurality of simulated ECG waveforms.

9. A training adapter for a defibrillator comprising:
an electrically insulated casing;
a controller disposed inside the casing;
a relay controlled by the controller;
a defibrillator electrode connector disposed on the casing;
a defibrillator connector electrically connecting the relay to a defibrillator;
an ECG simulator electrically connected to the relay opposite the defibrillator connector; and
a shunt resistor electrically connected to the relay opposite the defibrillator connector,
wherein the defibrillator electrode connector is electrically connected to the controller, and further wherein the controller operates the relay in response to a signal from the defibrillator electrode connector indicating that a pair of patient electrodes are positioned properly on a simulated patient,
thereby bypassing any electrical path from the defibrillator to the pair of patient electrodes.

10. The training adapter of claim 9, further comprising a user interface disposed outside the casing and in electrical communication with the ECG simulator and controller, wherein the user interface is operable to close the relay.

11. The training adapter of claim 9, further comprising a user interface disposed outside the casing and in electrical communication with the ECG simulator and controller, the user interface operable to select one of a plurality of simulated ECG waveforms and to display an operating status of the training adapter.

12. The training adapter of claim 11, where the user interface is a wireless remote control wirelessly connected to the controller and the ECG simulator.

13. The training adapter of claim 9, further comprising a pair of patient electrodes connected to the defibrillator electrode connector, wherein the pair of patient electrodes and the defibrillator connector are integral to the training adapter.

14. A method for using a defibrillator in a training mode, the steps comprising:
sensing the proper placement of electrodes on a simulated patient;
automatically connecting an ECG simulator to a defibrillator in response to the sensing step;
providing a simulated ECG signal from the ECG simulator to the defibrillator; and
shunting all defibrillation energy delivered by the defibrillator responsive to the providing step away from the electrodes.

15. The method of claim 14, further comprising the step of selecting the simulated ECG signal from one of a plurality of ECG signals including normal sinus rhythm, ventricular fibrillation, ventricular tachycardia, or asystole.

16. The method of claim 15, further comprising the steps of:
displaying the selected simulated ECG signal; and
displaying the progress of the training use of the defibrillator.

17. The method of claim 10, wherein the automatically connecting step further comprises a controller closing an electrical relay in response to a sensing signal from the sensing step, thereby electrically connecting the defibrillator to the ECG simulator and a shunt resistor.

18. The method of claim 17, further comprising operating the defibrillator in a defibrillation mode of operation.

19. The method of claim 18, further comprising the step of delivering a shock from the defibrillator to the shunt resistor in response to the providing step.

* * * * *